(12) United States Patent
Goebel

(10) Patent No.: US 6,613,439 B1
(45) Date of Patent: *Sep. 2, 2003

(54) ADHESION-PROMOTING COMPOSITION FOR BONDS BETWEEN PLASTIC AND OTHER MATERIALS

(75) Inventor: Roland Goebel, Jena (DE)

(73) Assignee: Ivoclar AG (LI)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/010,706

(22) Filed: Jan. 22, 1998

(30) Foreign Application Priority Data

Jan. 25, 1997 (DE) .......................... 197 02 704

(51) Int. Cl.$^7$ .................... B32B 17/06; B32B 15/04; C08J 7/06; C08K 5/5415; C09J 5/04

(52) U.S. Cl. ............. 428/429; 106/287.11; 106/287.13; 106/287.15; 106/287.16; 106/287.18; 106/287.19; 156/314; 156/329; 427/376.3; 427/376.4; 427/387; 427/388.1; 427/388.4; 427/389.7; 427/407.2; 427/409; 427/419.1; 427/419.8; 428/447; 428/450

(58) Field of Search ................ 106/287.11, 287.13, 106/287.15, 287.16, 287.19, 287.18; 427/376.3, 376.4, 387, 388.1, 388.4, 389.7, 407.2, 409, 419.1, 419.8; 428/429, 447, 450; 156/314, 329

(56) References Cited

U.S. PATENT DOCUMENTS

| 3,532,708 A | | 10/1970 | Blance | |
|---|---|---|---|---|
| 4,743,503 A | * | 5/1988 | Lin et al. | ................. 428/353 |
| 5,552,178 A | * | 9/1996 | Seo et al. | ..................... 427/64 |

FOREIGN PATENT DOCUMENTS

| CA | 1244182 | 11/1988 |
|---|---|---|
| CA | 1332662 | 10/1994 |
| EP | 0 017 937 A2 | 10/1980 |
| EP | 0 103 420 A2 | 3/1984 |
| EP | 0 507 177 A2 | 10/1992 |
| GB | 772 675 | 4/1957 |

* cited by examiner

Primary Examiner—D. S. Nakarani
(74) Attorney, Agent, or Firm—Nixon Peabody LLP

(57) ABSTRACT

An adhesion-promoting composition for bonds between plastic and other materials, such as metal, ceramic, glass ceramic and glass is described, which contains an alcoholate of titanium, of zirconium or of hafnium and allows production of strongly adhesive, moisture-stable and hydrolysis-resistant bonds.

75 Claims, No Drawings

ADHESION-PROMOTING COMPOSITION FOR BONDS BETWEEN PLASTIC AND OTHER MATERIALS

FIELD OF THE INVENTION

The invention relates to an adhesion-promoting composition for bonds between plastic and other materials, which is suitable for the permanent and moisture-stable bonding of, in particular, dental plastics with dental alloys.

BACKGROUND OF THE INVENTION

For the optimum aesthetic fashioning of prosthetic metal structures, such as crowns and bridges, it is necessary to provide the metal surface with a tooth-coloured plastic. The plastic used in this procedure usually comprises an organic matrix based on methacrylate and dimethacrylate monomers, an initiator system, an organic filler and colour pigments. Because of the extreme conditions encountered in the oral environment, the constant changes in moisture and temperature and the high degree of mechanical stress, mechanical anchorages for the securing of the plastic are not sufficient to permanently maintain even an only nearly satisfactory bond between the dental alloy and the veneer plastic. As a rule, therefore, formation of a marginal gap of 5 to 10 μm occurs between the alloy and the plastic after only a short time, the result of which can be a marked weakening of the bond to the point where the veneer is loosened. The loosening makes possible a corrosion of the metal in the region of the gap and this is accompanied by an unattractive discoloration of the veneer plastic.

Numerous suggestions have been made in recent years for the gap-free bonding of dental plastics with dental alloys. The basic principle of some of these procedures is that a silicate layer is applied to the metal surface (silicatization) in a first step and the surface is coated with a functional alkoxy silane (silanization) in a second step. The alkoxy silane, in most cases hydrolysed methacryloyloxypropyl trimethoxy silane, acts as a bonding member between the inorganic silicate layer and the dental plastic, which generally contains methacrylate. This effect is based on the fact that, on the one hand, the OH groups of the silane with the OH groups at the surface of the silicate layer are chemically bound by a condensation reaction to the silicate layer and, on the other hand, a binding to the matrix of the plastic takes place via the methacrylate group of the silane. The known procedures differ in the way in which the silicate layer is applied, while the application of the adhesion silane is virtually identical in all the procedures.

A method of applying a silicon dioxide layer to metal dental prosthesis parts by means of a high-frequency magnetron sputtering device is described in U.S. Pat. No. 4,364,731.

A procedure in which the silicate layer is applied by means of a flame hydrolysis process using tetraethoxy silane is disclosed in DE-C-34 03 894.

Moreover, a procedure in which a silicate/chromium oxide layer is applied to the surface of a dental alloy by a sol/gel solution and solidified by a subsequent heat treating process at 320° C. for 2 to 8 minutes is disclosed in DD-A-276 453.

A procedure in which the silicate coating takes place by means of a corundum jet process, adding a certain quantity of silicon dioxide having an average particle size of <5 μm to the sprayed corundum, is described in DE-A-38 02 043. Local energy densities, which are sufficient to melt the finely dispersed silicate particles onto the metal surface, occur in the area in which the corundum particles impact.

Finally, a procedure in which, instead of the inorganic silicate layer, an organic phenolic resin/acrylate/methacrylate layer serves as the bond layer, is described in DE-A-42 28 530.5.

With the described bond procedures, in particular with the sputtering process, the flame hydrolysis procedure and the sol/gel procedure, it is necessary, for the bond layer to adhere strongly to the surface of the alloy, to heat the latter to a temperature of about 300° C. However, such a high temperature proves disadvantageous with certain alloys, e.g. alloys with a copper content of >5%, as it leads to a change in the composition of the alloy at the surface. This also results in a reduction in adhesion and discoloration of the alloy. Moreover, the known procedures require a major outlay on apparatus, or the use of expensive chemicals, if they are to be carried out.

SUMMARY OF THE INVENTION

The object of the invention is therefore to provide an adhesion-promoting composition for bonds between plastic and other materials, which can be used with only a small outlay on apparatus and exposing the material to a small temperature stress, and which makes it possible to produce a strongly adhesive and moisture-stable bond layer and through the latter a permanent, high-strength connection, free of marginal gaps, between plastic and other materials.

This object is achieved by the adhesion-promoting composition according to claims 1 to 7. The invention also relates to the use of the composition according to claims 8 to 9, to a process for the production of bonds between plastic and other materials according to claims 10 to 15, and to the material according to claim 16 having a bond layer.

DETAILED DESCRIPTION OF THE INVENTION

The adhesion-promoting composition according to the invention for bonds between plastic and other materials is characterized by the fact that it contains (a) at least one alcoholate of titanium, of zirconium or of hafnium.

The alcoholates used are from time to time also described as esters of titanium, zirconium and hafnium.

The alcohol moiety of the alcoholates used according to the invention can be derived from aliphatic or aromatic alcohols.

Alcoholates derived from aliphatic $C_1$ to $C_5$ alcohols, such as in particular tetrabutyl titanate, tetrapropyl titanate, tetraisopropyl titanate or zirconium(IV) propylate, are preferred.

It is preferred that the composition also contains (b) at least one alkoxy silane having at least one further functional group. Coming into consideration as a further functional group are in particular a vinyl, methacryl, acryl, glycidyl or amino group, with combinations of different functional groups being also possible. The alkoxy silanes generally contain 1 to 3 alkoxy groups, with methoxy and ethoxy being preferred. Special examples of particularly suitable alkoxy silanes are vinyl-trimethoxy silane, γ-methacryloxypropyl trimethoxy silane, 3-glycidoxypropyl triethoxy silane and aminoethylaminopropyl trimethoxy silane.

Finally, it has also proved suitable that the composition also contains (c) a solvent for the alcoholate (a) and, if present, for the functional alkoxy silane (b). In view of the high reactivity of the alcoholates with water, anhydrous solvents are preferred. Acetone, acetic acid ethyl ester, isopropanol or hexane come into consideration in particular.

If a combination of alcoholate (a) and functional alkoxy silane (b) is used, then these can be applied jointly, e.g. in the form of a single-component solution, or successively, i.e. in the form of two solutions. The alcoholate and the alkoxy silane can be present together in the form of a packaging unit in which both components are present separate from each other. The two components can be released from such a unit immediately before use and e.g. mixed to give a single-component solution. Particularly preferred solutions have the following compositions:

Solution 1: 5 to 50 ml of a titanium alcoholate or zirconium alcoholate
100 ml solvent Solution 2: 5 to 10 ml functional alkoxy silane
100 ml solvent.

By mixing solutions 1 and 2, a solution 3 can be produced which can be used as a single-component solution.

Solution 3: 5 to 50 ml titanium alcoholate or zirconium alcoholate
5 to 10 ml functional alkoxy silane
200 ml solvent.

It has been shown that the composition according to the invention is outstandingly suitable for improving the bond between plastic and other materials, such as in particular metals, including alloys, ceramics, glass ceramics or glasses.

For this reason it is also preferably used as a dental material. With its help it is possible to provide dental alloys of very different compositions with a bond layer which, through its adhesion-promoting action, leads to a very good binding of the dental alloy to dental plastics. In addition to the production of e.g. plastic/metal bonds, metal can also be bonded to metal, with both metal materials being provided with the composition and joined to each other by using a dental adhesive. The bonds obtained show by high strength even after frequent exposure to temperature change and prolonged storage in water at elevated temperatures.

The composition according to the invention can also be preferably used as an adhesion promoter for paint coatings in mechanical engineering and body construction.

The process when producing bonds between plastic and other materials is that (i) the composition according to the invention is applied to the material and the alcoholate is hydrolysed and (ii) the plastic is applied to the material that has been provided with the composition.

If, as well as the alcoholate, alkoxy silane is present in the composition, then these two components can be applied either jointly, e.g. in the form of a single-component solution, or successively, e.g. in the form of separate solutions. In the latter case, the alcoholate is preferably applied first, and the alkoxy silane only afterwards.

Following the application of the composition in step (i) to the material, hydrolysis takes place and thus also condensation of the highly reactive titanium, zirconium or hafnium alcoholates by the OH groups present at the surface of the material or the water bound by chemisorption at the surface. Materials exposed to normal humidity regularly contain a proportion of surface OH groups or of water bound by chemisorption which is sufficient for the hydrolysis of the alcoholates to take place to an adequate extent. Finally, as a result of the hydrolysis and condensation, a $TiO_2$, $ZrO_2$ or $HfO_2$-containing layer forms which adheres strongly to the surface of the material.

In order to complete this reaction and remove the water and alcohol that have formed as a result of the reaction and any solvent that may be present, a heat treatment can be carried out, at a temperature of in particular less than 300° C., and preferably at temperatures between 100 and 200° C., after the composition has been applied. The temperature treatment is usually carried out only after any solvent present has substantially evaporated.

Through the simultaneous or optionally consecutive use of the functional alkoxy silane (b), silanization of the formed $TiO_2$, $ZrO_2$ or $HfO_2$-containing layer takes place. The functionality of the alkoxy silane makes possible the binding to the matrix of the plastic applied in stage (ii). It is possible to match the functionality of the alkoxy silane to the plastic selected in each case. Particularly preferred plastics are plastics used in the dental field and in particular plastics based on acrylates or methacrylates. The plastic is usually applied by application of a corresponding monomer mixture and its curing.

Compared with the state of the art, the following advantages are obtained with the composition according to the invention and the process according to the invention:

the applied inorganic bond layer prevents a water diffusion, weakening the bond, to the surface of the material, the solidification of the bond layer can take place at room temperature or through temperature treatment at temperatures of up to 200° C., with the result that there is no change weakening the bond, e.g. at alloy surfaces, the bond process according to the invention can be used regardless of the composition of alloys, the process according to the invention can be realized for only a small outlay on apparatus such as simple heat sources.

Finally, the invention also relates to a material based on metal, ceramic, glass ceramic or glass, which has a bond layer which can be obtained by the application, described above, of the compositions according to the invention to the surface of the material and hydrolysis of the alcoholate (a). Such materials are prepared for a later secure connection with plastic in an excellent manner.

Other advantageous embodiments of the invention and also in particular its use in dentistry are explained in the following examples.

EXAMPLES

The compression/shear strength values of alloy/plastic bonds or alloy/alloy bondings that are given in the following show the effectiveness of the present invention. The untreated surface serves as a comparison value for the strength of the bond (blank value). In all examples the surface of the materials used was corundum-blasted in accordance with to the state of the art (corundum particle size: 50 to 250 μm, jet pressure: 1 to 5 bar).

The compositions of the adhesion-promoting solutions 1, 2 and 3 that were used were as follows:

Solution 1: 100 ml tetraisopropyl titanate
900 ml acetic acid ethyl ester

Solution 2: 100 ml γ-methacryloxypropyl trimethoxy silane
900 ml acetone

Solution 3: 100 ml tetraisopropyl titanate 400 ml γ-methacryloxypropyl trimethoxy silane
500 ml acetic acid ethyl ester

Example 1

Alloy/Plastic Bond

Firstly, solution 1 was applied to the corundum-blasted surface of a selected alloy. After the solvent had evaporated, solution 2 was applied. The alloy with the two layers was then subjected to either a prolonged drying process at 25 to 80° C., preferably for 30 minutes at 50° C., or to a shorter temperature treatment at 100 to 200° C., preferably for 2 minutes at 150° C. When the single-component solution 3 was used instead of solution 1 and solution 2, drying and tempering were carried out in the same way after the application of this solution.

A methacrylate-based dental opacifier customary in the trade was then applied to the obtained bond layer and polymerized, after which the actual veneer plastic was modelled on by means of a metal ring (diameter: 5 mm, height: 2 mm) and likewise polymerized. After the removal of the metal ring, a plastic cylinder with a diameter of 5 mm and a height of 2 mm was situated on the alloy. The metal/plastic bond produced in this way was stored for 24 hours in distilled water and the strength of the bond was then tested in accordance with ISO standard 10477 in a compression/shearing test (rate of advance of the test machine: 1 mm min$^{-1}$). To enable simulation of the actual mechanical stresses taking place over the years in the mouth, the produced bonds were additionally subjected to temperature alternation stress (TAS) or boiled for 3 days. In the case of the temperature alternation stress, there were 5000 temperature alternations between the temperatures $t_1=5°$ C. and $t_2=55°$ C. The measured bond strengths for various dental alloys and dental plastics are given in Tables I and II.

In these, the quoted designations stand for the following materials:

Albabond=palladium alloy

Mainbond EH=gold alloy

Maingold SG=gold alloy

Hera GG=gold alloy

Titan=titanium alloy

Heraenium CE=cobalt/chromium alloy

Wiron 88=nickel alloy

The dental plastics were materials, customary in the trade, based on dimethacrylates.

TABLE I

Alloy/plastic bond
(Opacifier: Art-Glas opacifier (Kulzer), veneer plastic: Art-Glas (Kulzer))

Shearing strength [MPa]

| Dental alloy | Blank value | | | | Solution 1 + solution 2; 150° C., 2 min | | | |
|---|---|---|---|---|---|---|---|---|
| | 24 h, 37° C. | 5000, TAS | 1 d boiled | 3 d boiled | 24 h, 37° C. | 5000, TAS | 1 d boiled | 3 d boiled |
| Albabond | 8.6 | 5.8 | 2.1 | 1.4 | 25.7 | 23.9 | 22.1 | 14.3 |
| Mainbond EH | 10.4 | 6.2 | 2.4 | 1.1 | 28.3 | 27.6 | 23.8 | 16.7 |
| Maingold SG | 10.0 | 6.4 | 2.0 | 0.8 | 27.1 | 25.8 | 21.3 | 15.1 |
| Hera GG | 9.8 | 6.0 | 2.2 | 1.3 | 26.8 | 25.3 | 20.7 | 14.5 |
| Titan | 11.0 | 6.5 | 1.8 | 1.1 | 28.7 | 27.0 | 23.4 | 16.9 |
| Heraenium CE | 9.2 | 5.8 | 1.5 | 0.7 | 26.0 | 24.3 | 21.0 | 13.7 |
| Wiron 88 | 8.8 | 5.5 | 1.6 | 0.8 | 25.3 | 23.8 | 20.2 | 13.2 |

TABLE II

Alloy/plastic bond
(Metal alloy: Mainbond EH; Opacifier: Visio-Gem-opacifier (Espe))

Shearing strength [MPa]

| Dental plastic | Blank value | | | | Solution 1 + solution 2; 150° C., 2 min | | | |
|---|---|---|---|---|---|---|---|---|
| | 24 h, 37° C. | 5000, TAS | 1 d boiled | 3 d boiled | 24 h, 37° C. | 5000, TAS | 1 d boiled | 3 d boiled |
| Visio-Gem (Espe) | 8.2 | 6.5 | 2.1 | 1.1 | 24.2 | 21.5 | 19.2 | 13.4 |
| Art-Glass (Kulzer) | 10.8 | 7.8 | 2.6 | 1.7 | 29.1 | 28.3 | 24.0 | 16.2 |
| Tetric (Vivadent) | 11.2 | 9.2 | 2.2 | 1.5 | 27.6 | 26.0 | 21.6 | 14.5 |
| Z 100 (3M) | 12.0 | 9.5 | 2.9 | 1.9 | 29.8 | 28.0 | 25.2 | 17.0 |
| Prodigy (Voco) | 9.2 | 7.3 | 2.0 | 1.8 | 26.7 | 25.0 | 22.1 | 14.2 |
| Polofil | 8.2 | 6.8 | 1.7 | 1.3 | 25.5 | 22.1 | 21.0 | 13.5 |

The compression/shear strength measurements of the alloy/plastic bonds (Tables I and II) show that, after the 24-hour storage in water at 37° C. and the 5000 alternating-load cycles with the solutions according to the invention, an almost 200% increase in bond strength is achieved compared with untreated alloy surfaces that have only been corundum-blasted. The difference between a treated surface and an untreated surface becomes even clearer if the alloy/plastic bonds are subjected to the extreme boiling test. With the surface that had merely been corundum-blasted, there was only an extremely small adhesion of the plastic to the surface of the alloy with 1 to 2 MPa, whereas with the solution according to the invention adequately high adhesion values of 13 to 17 MPas were still measured.

The list in Table I of the dental alloys with their very different compositions, from alloys with a high gold content to alloys of base metals, also makes it clear that the adhesion-promoting action of the produced bond layer does not depend on the composition of the alloy.

Example 2

Alloy/Alloy Bondings

In this example, dental alloys were bonded to each other with the help of dental plastics. The procedure for the preparation of the alloy surfaces was analogous to that described in example 1. The overlap length of the bonding was 10 mm and the adhesion surface was 100 mm². The bonded alloy specimens were boiled for up to 5 days. The ascertained shearing strengths are given in Table III below.

Chemiace, Brilliant enamel kit, Palavit 55 and Twinlook are commercial dental plastics. Pattex Stabilit is an all-purpose adhesive customary in the trade.

TABLE III

| | Alloy/alloy bondings (Metal alloy: Wiron 88) | | | |
|---|---|---|---|---|
| | Blank value | | Shearing strength [MPa] Solution 1 + solution 2, 150° C., 4 min | |
| Dental plastic | 24 h, 37° C. | 5 d boiled | 24 h, 37° C. | 5d boiled |
| Chemiace (Sun Medical) | 12.3 | 5.5 | 22.4 | 18.9 |
| Brilliant enamel kit (Coltene) | 11.8 | 4.4 | 20.1 | 16.8 |
| Palavit 55 (Kulzer) | 10.2 | 4.8 | 21.2 | 18.0 |
| Twinlook (Kulzer) | 11.4 | 5.1 | 22.6 | 18.9 |
| Pattex Stabilit (Epoxy resin) (Henkel) | 13.4 | 6.8 | 24.7 | 20.7 |

The measured values listed in Table III show a picture similar to that for the alloy/plastic bonds. In view of the metal/metal bonding, entry of water can take place only via the thin bonding joint (50–150 μm). On the untreated surface, the bond values fall to half as a result of the boiling. With the solution according to the invention, the bond strength achieved in the case of the bondings was double compared with the untreated surface. The boiling treatment caused only a slight fall of some 20% in adhesive strength.

Through the invention, a strongly adhesive, moisture-stable and hydrolysis-resistant bond layer is available which is suitable for the most varied bonds and is not restricted just to use in dentistry. An equally advantageous use of the solutions according to the invention is for the production of bond layers for paint coating in mechanical engineering and body construction. The durability of a paint coating or cementing is thereby greatly extended even under extreme moist conditions.

What is claimed is:

1. An adhesion-promoting anhydrous composition comprising:
   (a) at least one alcoholate of titanium, zirconium, or hafnium; and
   (b) at least one alkoxy silane having at least one further functional group.

2. The composition according to claim 1, wherein the alcoholate (a) is tetrabutyl titanate, tetrapropyl titanate, tetraisopropyl titanate or zirconium (IV) propylate.

3. The composition according to claim 1 wherein the at least one further functional group of the alkoxy silane (b) comprises a vinyl, methacryl, acryl, glycidyl or amino group.

4. The composition according to claim 1, wherein the alkoxy silane (b) is a vinyl-trimethoxy silane, γ-methacryloxypropyl trimethoxy silane, 3-glycidoxypropyl triethoxy silane or aminoethylaminopropyl trimethoxy silane.

5. A material comprising metal, ceramic, glass ceramic or glass, which has a bond layer made from applying the composition according to claim 1, to the surface of the material and hydrolyzing the at least one alcoholate (a).

6. The composition according to claim 1, further comprising a solvent (c).

7. The composition according to claim 6, wherein the solvent (c) is acetone, acetic acid ethyl ester, isopropanol or hexane.

8. A process for bonding a first material to a second material comprising:
   applying an anhydrous composition comprising (a) at least one alcoholate of titanium, zirconium, or hafnium and (b) at least one alkoxy silane having at least one further functional group to a first material, wherein the first material is a metal, ceramic, glass ceramic, glass, or dental metal alloy; and
   bonding the first material to a second material, wherein the second material is a plastic material having a matched functionality with the functionality of the at least one alkoxy silane.

9. The process according to claim 8, wherein the plastic material is acrylate plastic or methacrylate plastic.

10. The process according to claim 8, further comprising subjecting the coated first material to a heat treatment.

11. The process according to claim 10, wherein the heat treatment is carried out at a temperature of from 100° C. to 200° C.

12. The process according to claim 8, wherein the anhydrous composition further comprises a solvent.

13. The process according to claim 12, wherein the solvent is acetone, acetic acid ethyl ester, isopropanol, or hexane.

14. The process according to claim 8, wherein the alcoholate is tetrabutyl titanate, tetrapropyl titanate, tetraisopropyl titanate, or zirconium (IV) propylate.

15. The process according to claim 8, wherein the at least one further functional group of the alkoxy silane comprises a vinyl, methacryl, acryl, glycidyl, or amino group.

16. The process according to claim 8, wherein the alkoxy silane is a vinyl-trimethoxy silane, γ-methacryloxypropyl trimethoxy silane, 3-glycidoxypropyl triethoxy silane, or aminoethylaminopropyl trimethoxy silane.

17. The product produced according to the process of claim 8.

18. A process for bonding a first material to a second material comprising:
   applying an anhydrous composition comprising (a) at least one alcoholate of titanium, zirconium, or hafnium and (b) at least one alkoxy silane having at least one further functional group to a first material, wherein the first material is a metal, ceramic, glass ceramic, glass, or dental metal alloy; and bonding the first material to a second material using a dental adhesive, wherein the second material is a metal, ceramic, glass ceramic, glass, or dental metal alloy.

19. The process according to claim 18, further comprising subjecting the coated first material to a heat treatment.

20. The process according to claim 19, wherein the heat treatment is carried out at a temperature of from 100° C. to 200° C.

21. The process according to claim 18, wherein the anhydrous composition further comprises a solvent.

22. The process according to claim 21, wherein the solvent is acetone, acetic acid ethyl ester, isopropanol, or hexane.

23. The process according to claim 18, wherein the alcoholate is tetrabutyl titanate, tetrapropyl titanate, tetraisopropyl titanate, or zirconium (IV) propylate.

24. The process according to claim 18, wherein the at least one further functional group of the alkoxy silane comprises a vinyl, methacryl, acryl, glycidyl, or amino group.

25. The process according to claim 18, wherein the alkoxy silane is a vinyl-trimethoxy silane, γ-methacryloxypropyl trimethoxy silane, 3-glycidoxypropyl triethoxy silane, or aminoethylaminopropyl trimethoxy silane.

26. The product produced according to the process of claim 18.

27. A process for bonding a first material to a second material comprising:

applying an anhydrous composition comprising at least one alcoholate of titanium, zirconium, or hafnium to a first material, wherein the first material is a metal, ceramic, glass ceramic, glass, or dental metal alloy; and bonding the first material to a second material, wherein the second material is a plastic material.

28. The process according to claim 27, wherein the plastic material is acrylate plastic or methacrylate plastic.

29. The process according to claim 27, further comprising subjecting the coated first material to a heat treatment.

30. The process according to claim 29, wherein the heat treatment is carried out at a temperature of from 100° C. to 200° C.

31. The process according to claim 27, wherein the anhydrous composition further comprises a solvent.

32. The process according to claim 31, wherein the solvent is acetone, acetic acid ethyl ester, isopropanol, or hexane.

33. The process according to claim 27, wherein the alcoholate is tetrabutyl titanate, tetrapropyl titanate, tetraisopropyl titanate, or zirconium (IV) propylate.

34. The product produced according to the process of claim 27.

35. A process for bonding a first material to a second material comprising:

applying an anhydrous composition comprising at least one alcoholate of titanium, zirconium, or hafnium to a first material, wherein the first material is a metal, ceramic, glass ceramic, glass, or dental metal alloy; and bonding the first material to a second material using a dental adhesive, wherein the second material is a metal, ceramic, glass ceramic, glass, or dental metal alloy.

36. The process according to claim 35, further comprising subjecting the coated first material to a heat treatment.

37. The process according to claim 36, wherein the heat treatment is carried out at a temperature of from 100° C. to 200° C.

38. The process according to claim 35, wherein the anhydrous composition further comprises a solvent.

39. The process according to claim 38, wherein the solvent is acetone, acetic acid ethyl ester, isopropanol, or hexane.

40. The process according to claim 35, wherein the alcoholate is tetrabutyl titanate, tetrapropyl titanate, tetraisopropyl titanate, or zirconium (IV) propylate.

41. The product produced according to the process of claim 35.

42. A process for bonding a first material to a second material comprising:

applying (a) an anhydrous solution comprising at least one alcoholate of titanium, zirconium, or hafnium and (b) a solution comprising at least one alkoxy silane having at least one further functional group to a first material, wherein the first material is a metal, ceramic, glass ceramic, glass, or dental metal alloy; and bonding the first material to a second material, wherein the second material is a plastic material having a matched functionality with the functionality of the at least one alkoxy silane.

43. The process according to claim 42, wherein the plastic material is acrylate plastic or methacrylate plastic.

44. The process according to claim 42, further comprising subjecting the coated first material to a heat treatment.

45. The process according to claim 44, wherein the heat treatment is carried out at a temperature of from 100° C. to 200° C.

46. The process according to claim 42, wherein solution (a) further comprises a solvent.

47. The process according to claim 46, wherein the solvent is acetone, acetic acid ethyl ester, isopropanol, or hexane.

48. The process according to claim 42, wherein solution (b) further comprises a solvent.

49. The process according to claim 48, wherein the solvent is acetone, acetic acid ethyl ester, isopropanol, or hexane.

50. The process according to claim 42, wherein the alcoholate is tetrabutyl titanate, tetrapropyl titanate, tetraisopropyl titanate, or zirconium (IV) propylate.

51. The process according to claim 42, wherein the at least one further functional group of the alkoxy silane comprises a vinyl, methacryl, acryl, glycidyl, or amino group.

52. The process according to claim 42, wherein the alkoxy silane is a vinyl-trimethoxy silane, γ-methacryloxypropyl trimethoxy silane, 3-glycidoxypropyl triethoxy silane, or aminoethylaminopropyl trimethoxy silane.

53. The product produced according to the process of claim 42.

54. A process for bonding a first material to a second material comprising:

applying (a) an anhydrous solution comprising at least one alcoholate of titanium, zirconium, or hafnium and (b) a solution comprising at least one alkoxy silane having at least one further functional group to a first material, wherein the first material is a metal, ceramic, glass ceramic, glass, or dental metal alloy; and bonding the first material to a second material using a dental adhesive, wherein the second material is a metal, ceramic, glass ceramic, glass, or dental metal alloy.

55. The process according to claim 54, further comprising subjecting the coated first material to a heat treatment.

56. The process according to claim 55, wherein the heat treatment is carried out at a temperature of from 100° C. to 200° C.

57. The process according to claim 54, wherein solution (a) further comprises a solvent.

58. The process according to claim 57, wherein the solvent is acetone, acetic acid ethyl ester, isopropanol, or hexane.

59. The process according to claim 54, wherein solution (b) further comprises a solvent.

60. The process according to claim 59, wherein the solvent is acetone, acetic acid ethyl ester, isopropanol, or hexane.

61. The process according to claim 54, wherein the alcoholate is tetrabutyl titanate, tetrapropyl titanate, tetraisopropyl titanate, or zirconium (IV) propylate.

62. The process according to claim 54, wherein the at least one further functional group of the alkoxy silane comprises a vinyl, methacryl, acryl, glycidyl, or amino group.

63. The process according to claim 54, wherein the alkoxy silane is a vinyl-trimethoxy silane, γ-methacryloxypropyl trimethoxy silane, 3-glycidoxypropyl triethoxy silane, or aminoethylaminopropyl trimethoxy silane.

64. The product produced according to the process of claim 54.

65. A process for bonding a first material to a second material comprising:
  applying an anhydrous first composition comprising at least one alcoholate of, titanium, zirconium, or hafnium to the surface of a first material, wherein the first material is a metal, ceramic, glass ceramic, glass, or dental metal alloy;
  hydrolyzing and condensing the at least one alcoholate to produce a coating adhering on the surface of the first material;
  silanizing the first material coating by applying to the first material a second composition comprising at least one alkoxy silane having at least one further functional group; and
  bonding the first material to a second material, wherein the second material is a plastic material having a matched functionality with the functionality of the at least one alkoxy silane.

66. The process according to claim 65, wherein the alcoholate is tetrabutyl titanate, tetrapropyl titanate, tetraisopropyl titanate, or zirconium (IV) propylate.

67. The process according to claim 65, wherein the at least one further functional group of the alkoxy silane comprises a vinyl, methacryl, acryl, glycidyl, or amino group.

68. The process according to claim 65, wherein the alkoxy silane is a vinyl-trimethoxy silane, γ-methacryloxypropyl trimethoxy silane, 3-glycidoxypropyl triethoxy silane, or aminoethylaminopropyl trimethoxy silane.

69. The process according to claim 65, further comprising subjecting the coated first material to a heat treatment.

70. The process according to claim 69, wherein the heat treatment is carried out at a temperature of from 100° C. to 200° C.

71. The process according to claim 65, wherein the first composition further comprises a solvent.

72. The process according to claim 71, wherein the solvent is acetone, acetic acid ethyl ester, isopropanol, or hexane.

73. The process according to claim 65, wherein the second composition further comprises a solvent.

74. The process according to claim 73, wherein the solvent is acetone, acetic acid ethyl ester, isopropanol, or hexane.

75. The product produced according to the process of claim 65.

\* \* \* \* \*